(12) United States Patent
Weaver (10) Patent No.: US 10,957,493 B2
(45) Date of Patent: Mar. 23, 2021

(54) WET ELECTROLYTIC CAPACITOR FOR AN IMPLANTABLE MEDICAL DEVICE

(71) Applicant: AVX Corporation, Fountain Inn, SC (US)

(72) Inventor: Mitchell D. Weaver, Simpsonville, SC (US)

(73) Assignee: AVX Corporation, Fountain Inn, SC (US)

( * ) Notice: Subject to any disclaimer, the term of this patent is extended or adjusted under 35 U.S.C. 154(b) by 9 days.

(21) Appl. No.: 16/208,950

(22) Filed: Dec. 4, 2018

(65) Prior Publication Data

US 2019/0172654 A1    Jun. 6, 2019

Related U.S. Application Data

(60) Provisional application No. 62/594,611, filed on Dec. 5, 2017.

(51) Int. Cl.
| | | |
|---|---|---|
| *H01G 9/145* | (2006.01) | |
| *H01G 9/052* | (2006.01) | |
| *H01G 9/02* | (2006.01) | |
| *A61N 1/05* | (2006.01) | |
| *H01G 9/08* | (2006.01) | |
| *H01G 9/035* | (2006.01) | |

(Continued)

(52) U.S. Cl.
CPC ............ *H01G 9/145* (2013.01); *A61N 1/05* (2013.01); *A61N 1/3975* (2013.01); *H01G 9/02* (2013.01); *H01G 9/035* (2013.01); *H01G 9/042* (2013.01); *H01G 9/0525* (2013.01); *H01G 9/08* (2013.01); *A61N 1/3956* (2013.01)

(58) Field of Classification Search
CPC .......... H01G 9/145; H01G 9/02; H01G 9/035; H01G 9/042; H01G 9/0525; H01G 9/08; A61N 1/05; A61N 1/3975; A61N 1/3956
See application file for complete search history.

(56) References Cited

U.S. PATENT DOCUMENTS

| | | | |
|---|---|---|---|
| 5,111,327 A | 5/1992 | Blohm et al. | |
| 5,369,547 A | 11/1994 | Evans | |

(Continued)

FOREIGN PATENT DOCUMENTS

| | | | |
|---|---|---|---|
| EP | 1 667 178 A1 | 6/2006 | |
| WO | WO 2009/048173 A1 | 4/2009 | |
| WO | WO 2013/186970 A1 | 12/2013 | |

OTHER PUBLICATIONS

Pozdeev-Freeman et al., "Critical oxygen content in porous anodes of solid tantalum capacitors," *Journal of Materials Science: Materials in Electronics*, vol. 9, 1998, pp. 309-311.

(Continued)

*Primary Examiner* — Michael P McFadden
(74) *Attorney, Agent, or Firm* — Dority & Manning, P.A.

(57) ABSTRACT

A wet electrolytic capacitor is provided. The capacitor comprises an anode that comprises an anodically oxidized pellet formed from a pressed and sintered valve metal powder, a cathode that comprises a metal substrate coated with a conductive coating, a microporous membrane that is positioned between the anode and cathode and contains an olefin polymer having a weight-average molecular weight of about 1,000,000 grams per mole or more, and a fluidic working electrolyte in communication with the anode and the cathode.

23 Claims, 2 Drawing Sheets

(51) Int. Cl.
*H01G 9/042* (2006.01)
*A61N 1/39* (2006.01)

(56) References Cited

U.S. PATENT DOCUMENTS

| | | | |
|---|---|---|---|
| 5,457,862 A | 10/1995 | Sakata et al. | |
| 5,473,503 A | 12/1995 | Sakata et al. | |
| 5,716,511 A | 2/1998 | Melody et al. | |
| 5,729,428 A | 3/1998 | Sakata et al. | |
| 5,812,367 A | 9/1998 | Kudoh et al. | |
| 6,162,345 A | 12/2000 | Kinard et al. | |
| 6,197,252 B1 | 3/2001 | Bishop et al. | |
| 6,231,993 B1 | 5/2001 | Stephenson et al. | |
| 6,261,434 B1 | 7/2001 | Melody et al. | |
| 6,267,861 B1 | 7/2001 | Kinard et al. | |
| 6,346,185 B1 | 2/2002 | Kinard et al. | |
| 6,430,026 B1 | 8/2002 | Nagato et al. | |
| 6,594,140 B1 | 7/2003 | Evans et al. | |
| 6,635,729 B1 | 10/2003 | Groenendaal et al. | |
| 6,671,167 B2 | 12/2003 | Araki et al. | |
| 6,674,635 B1 | 1/2004 | Fife et al. | |
| 6,786,951 B2 | 9/2004 | He et al. | |
| 6,801,424 B1 | 10/2004 | Nielsen et al. | |
| 6,967,828 B2 | 11/2005 | Miltich et al. | |
| 6,985,352 B2 | 1/2006 | Norton | |
| 6,987,663 B2 | 1/2006 | Merker et al. | |
| 6,995,971 B2 | 2/2006 | Norton et al. | |
| 7,085,126 B2 | 8/2006 | Muffoletto et al. | |
| 7,090,762 B2 | 8/2006 | Tripp et al. | |
| 7,150,776 B2 | 8/2006 | Gloss et al. | |
| 7,169,284 B1 | 1/2007 | Jiang et al. | |
| 7,224,575 B2 * | 5/2007 | Sherwood | H01G 9/0032 361/508 |
| 7,242,572 B2 | 7/2007 | Norton et al. | |
| 7,248,462 B2 | 7/2007 | Melody et al. | |
| 7,256,982 B2 | 8/2007 | Lesner et al. | |
| 7,262,511 B2 | 8/2007 | Kundalgurki | |
| 7,431,751 B2 | 10/2008 | Shekhter et al. | |
| 7,483,260 B2 | 1/2009 | Ziarniak et al. | |
| 7,515,396 B2 | 4/2009 | Biler | |
| 7,531,010 B1 | 5/2009 | Feger et al. | |
| 7,544,218 B2 | 6/2009 | Norton et al. | |
| 7,589,956 B2 | 9/2009 | Norton et al. | |
| 7,667,954 B2 | 2/2010 | Lessner et al. | |
| 7,678,259 B2 | 3/2010 | Melody et al. | |
| 7,710,713 B2 | 5/2010 | Restorff et al. | |
| 7,727,372 B2 | 6/2010 | Liu et al. | |
| 7,731,893 B2 | 6/2010 | Freeman et al. | |
| 7,875,087 B2 | 1/2011 | Norton et al. | |
| 7,879,217 B2 | 2/2011 | Goad et al. | |
| 7,952,853 B2 | 5/2011 | Viste et al. | |
| 8,199,459 B2 | 6/2012 | Nielsen et al. | |
| 8,203,827 B2 | 6/2012 | Karnik | |
| 8,313,538 B2 | 11/2012 | Merker et al. | |
| 8,313,621 B2 | 11/2012 | Goad et al. | |
| 8,477,479 B2 | 7/2013 | Pease et al. | |
| 8,675,348 B2 | 3/2014 | Viste et al. | |
| 8,687,347 B2 | 4/2014 | Bates et al. | |
| 9,053,854 B2 | 6/2015 | Petrzilek et al. | |
| 9,105,401 B2 | 8/2015 | Dreissig et al. | |
| 9,236,192 B2 | 1/2016 | Biler et al. | |
| 9,384,901 B2 | 7/2016 | Weaver | |
| 9,620,293 B2 | 4/2017 | Djebara et al. | |
| 9,620,294 B2 | 4/2017 | Djebara et al. | |
| 9,786,440 B2 | 10/2017 | Weaver et al. | |
| 10,056,592 B2 | 8/2018 | Krishnamoorthy et al. | |
| 10,153,472 B2 | 12/2018 | Li et al. | |
| 10,290,430 B2 | 5/2019 | Djebara et al. | |
| 10,340,492 B2 | 7/2019 | Inatomi et al. | |
| 2004/0243183 A1 | 12/2004 | Norton et al. | |
| 2008/0151474 A1 * | 6/2008 | Ziarniak | H01G 9/04 361/529 |
| 2010/0175235 A1 * | 7/2010 | Nielsen | H01M 2/361 29/25.03 |
| 2013/0242467 A1 * | 9/2013 | Biler | C09D 5/4476 361/504 |
| 2016/0351339 A1 * | 12/2016 | Uher | H01G 9/0036 |
| 2017/0263384 A1 | 9/2017 | Naito et al. | |
| 2018/0133493 A1 | 5/2018 | Petrzilek et al. | |
| 2018/0137985 A1 | 5/2018 | Petrzilek et al. | |
| 2018/0137989 A1 | 5/2018 | Petrzilek et al. | |

OTHER PUBLICATIONS

International Search Report and Written Opinion for PCT/US2018/063828 dated Mar. 22, 2019, 13 pages.

* cited by examiner

WET ELECTROLYTIC CAPACITOR FOR AN IMPLANTABLE MEDICAL DEVICE

CROSS REFERENCE TO RELATED APPLICATION

The present application claims filing benefit of U.S. Provisional Patent Application Ser. No. 62/594,611 having a filing date of Dec. 5, 2017, which is incorporated herein by reference in its entirety.

BACKGROUND OF THE INVENTION

High voltage electrolytic capacitors are often employed in implantable medical devices. These capacitors are required to have a high energy density because it is desirable to minimize the overall size of the implanted device. This is particularly true of an implantable cardioverter defibrillator ("ICD"), also referred to as an implantable defibrillator, because the high voltage capacitors used to deliver the defibrillation pulse can occupy as much as one third of the ICD volume. ICDs typically use two to four electrolytic capacitors in series to achieve the desired high voltage for shock delivery. In some cases, these capacitors may be "wet tantalum" capacitors that contain a sintered tantalum anode, a conductive cathode, and a separator that electrically isolates the anode and cathode while still allowing for the passage of a working electrolyte therethrough. Conventional separators are often been formed from nonwoven fabrics that are impregnated with a surfactant to improve wettability. In addition to being costly, however, the use of surfactants can be problematic in that the wettability of the separator is susceptible to being reduced over time. As such, a need currently exists for an improved wet electrolytic capacitor for use in implantable medical devices, such as defibrillators.

SUMMARY OF THE INVENTION

In accordance with one embodiment of the present invention, a wet electrolytic capacitor is disclosed. The capacitor comprises an anode that comprises an anodically oxidized pellet formed from a pressed and sintered valve metal powder, a cathode that comprises a metal substrate coated with a conductive coating, a microporous membrane that is positioned between the anode and cathode and contains an olefin polymer having a weight-average molecular weight of about 1,000,000 grams per mole or more, and a fluidic working electrolyte in communication with the anode and the cathode.

Other features and aspects of the present invention are set forth in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Repeat use of references characters in the present specification and drawings is intended to represent same or analogous features or elements of the invention.

DETAILED DESCRIPTION OF REPRESENTATIVE EMBODIMENTS

It is to be understood by one of ordinary skill in the art that the present discussion is a description of exemplary embodiments only, and is not intended as limiting the broader aspects of the present invention, which broader aspects are embodied in the exemplary construction.

Generally speaking, the present invention is directed to a wet electrolytic capacitor that contains at least one anode formed from an anodically oxidized sintered porous pellet, at least one cathode that contains a conductive coating disposed on a metal substrate, and a working electrolyte in communication with the anode and cathode. The capacitor also includes at least one microporous membrane (e.g., sheet, film, fabric, etc.) that is positioned between the anode and cathode. Through selective control over its thickness and the particular material from which it is formed, the present inventor has discovered that the resulting membrane can function effectively as a separator for the capacitor without the need for conventional surfactants. The microporous membrane, for instance, generally contains an olefin polymer (e.g., homopolymer or copolymer) having a relatively high weight-average molecular weight ($M_w$), such as about 1,000,000 grams per mole (g/mol) or more, In some embodiments 3,000,000 g/mol or more, in some embodiments about 5,000,000 g/mol or more, and in some embodiments, from about 6,000,000 to about 20,000,000 g/mol. In one particular embodiment, the olefin polymer is an ethylene polymer (also known as ultra-high molecular weight polyethylene ("UHMWPE")). Due in part to the materials from which it is formed and the manner in which it is made, it has been discovered that the membrane can possess a high degree of physical strength and integrity in both the machine and transverse directions. For example, the tensile strength in the machine direction ("MD") and/or transverse direction ("TD") may be about 30 Megapascals ("MPa") or more, in some embodiments about 50 MPa or more, and in some embodiments, from about 80 to about 250 MPa, such as determined in accordance with ASTM D882-12 at a temperature of about 23° C. Among other things, such a high degree of multi-directional strength can allow relatively small thicknesses to be employed without sacrificing performance. In this regard, the membrane may have a thickness of about 100 micrometers or less, in some embodiments from about 5 to about 80 micrometers, and in some embodiments, from about 10 to about 60 micrometers. Notably, the ratio of the total thickness of the capacitor to the thickness of the microporous membrane may also be relatively large, such as about 5 or more, in some embodiments about 10 or more, in some embodiments about 20 or more, and in some embodiments, from about 30 to about 150.

Various embodiments of the present invention will now be described in more detail.

I. Anode

The anode may be formed from a valve metal powder that contains a valve metal (i.e., metal that is capable of oxidation) or valve metal-based compound, such as tantalum, niobium, aluminum, hafnium, titanium, alloys thereof, oxides thereof, nitrides thereof, and so forth. For example, the valve metal powder may contain an electrically conductive oxide of niobium, such as niobium oxide having an atomic ratio of niobium to oxygen of 1:1.0±1.0, in some embodiments 1:1.0±0.3, in some embodiments 1:1.0±0.1, and in some embodiments, 1:1.0±0.05. The niobium oxide may be $NbO_{0.7}$, $NbO_{1.0}$, $NbO_{1.1}$, and $NbO_2$.

If desired, the valve metal powder may be formed by reacting an oxide of a valve metal compound with a reducing agent that contains a metal having a relatively high oxidation state (e.g., magnesium). The valve metal oxide is typically a tantalum and/or niobium oxide capable of being reduced, such as $Ta_2O_x$ ($x \leq 5$) (e.g., $Ta_2O_5$) or $Nb_2O_x$ ($x \leq 5$) (e.g., $Nb_2O_5$). The reducing agent may be provided in a gaseous, liquid, or solid state, and may also be in the form of the metal, as well as alloys or salts thereof. In one embodiment, for instance, a halide salt (e.g., chloride, fluoride, etc.) may be employed. If desired, other components may also be added before, during, or after the reaction, such as dopants, alkali metals, etc. The reduction of the oxide is typically carried out at a temperature of from about 400° C. to about 1200° C., and in some embodiments, from about 600° C. to about 1000° C., for about 20 to about 300 minutes. Heating may be carried out in a reactor under an inert atmosphere (e.g., argon or nitrogen atmosphere) so that a molten bath is formed. Suitable reactors may include, for instance, vertical tube furnaces, rotary kilns, fluid bed furnaces, multiple hearth furnaces, self-propagation high-temperature synthesis reactors, etc. The reactor may be maintained under inert gas until that the mass in the reaction vessel is cooled to ambient temperature. Additional details of such a reduction reaction may be described in U.S. Patent Publication Nos. 2003/0110890 to He, et al. and 2004/0163491 to Shekhter, et al.

After the reduction, the product may be cooled, crushed, and washed to remove excess impurities or reactants. The washing solution may include, for instance, a mineral acid and water. If desired, the powder may be subjected to additional treatment to remove any tantalates/niobates (e.g., magnesium tantalate) that may have formed during the reaction. In one embodiment, for instance, one technique for removing the tantalates/niobates involves heating the powder under vacuum at a temperature of from about 1100° C. to about 1400° C. for about 15 minutes to about 6 hours. Likewise, another technique for removing the tantalates/niobates involves heating the powder at a temperature of from about 800° C. to about 1300° C. in the presence of a getter material, such as magnesium, calcium and/or aluminum, for about 15 minutes to about 6 hours. Such techniques may be described in more detail in U.S. Pat. No. 7,431,751 to Shekhter, et al. Although not required, the powder may be subjected to additional refining steps as is known in the art, such as doping, deoxidizing, etc.

Regardless of the particular steps employed, the resulting powder has a variety of beneficial properties. The powder may, for example, be a free-flowing, finely divided powder that contains primary particles having a three-dimensional shape, such as a nodular or angular shape. Such particles are not generally flat and thus have a relatively low "aspect ratio", which is the average diameter or width of the particles divided by the average thickness ("D/T"). For example, the aspect ratio of the particles may be about 4 or less, in some embodiments about 3 or less, and in some embodiments, from about 1 to about 2. The powder may also have a relatively high specific surface area, such as about 1 square meter per gram ("$m^2/g$") or more, in some embodiments about 2 $m^2/g$ or more, and in some embodiments, from about 4 to about 30 $m^2/g$. The term "specific surface area" generally refers to surface area as determined by the physical gas adsorption (B.E.T.) method of Bruanauer, Emmet, and Teller, Journal of American Chemical Society, Vol. 60, 1938, p. 309, with nitrogen as the adsorption gas. The test may be conducted with a MONOSORB® Specific Surface Area Analyzer available from QUANTACHROME Corporation, Syosset, N.Y., which measures the quantity of adsorbate nitrogen gas adsorbed on a solid surface by sensing the change in thermal conductivity of a flowing mixture of adsorbate and inert carrier gas (e.g., helium).

The primary particles of the powder may also have a median size (D50) of from about 5 to about 1000 nanometers, and in some embodiments, from about 10 to about 500 nanometers, such as using a laser particle size distribution analyzer made by BECKMAN COULTER Corporation (e.g., LS-230), optionally after subjecting the particles to an ultrasonic wave vibration of 70 seconds. Due to its high surface area and low particle size, the powder may have a high specific charge, such as greater than about 15,000 microFarads*Volts per gram ("µF*V/g"), in some embodiments from about 18,000 to about 60,000 µF*V/g, and in some embodiments, from about 20,000 to about 50,000 µF*V/g. As is known in the art, the specific charge may be determined by multiplying capacitance by the anodizing voltage employed, and then dividing this product by the weight of the anodized electrode body. Despite the use of such high specific charge powders with three-dimensional particles, the ability to achieve high voltages can be achieved through the manner in which the powder is formed. More particularly, it is believed that the particular reduction process employed can achieve "sinter necks" between adjacent agglomerated particles that are relatively large in size. Sinter necks are the small cross-sectional area of the electrical path within the metal structure. Typically, the sinter necks have a size of about 200 nanometers or more, in some embodiments about 250 nanometers or more, and in some embodiments, from about 300 to about 800 nanometers. Because the necks are relatively large in size, the dielectric layer in the vicinity of the neck is more likely not to fail at high forming voltages.

The powder (as well as the anode) may also have a relatively low alkali metal, carbon, and oxygen content. For example, the powder may have no more than about 50 ppm carbon or alkali metals, and in some embodiments, no more than about 10 ppm carbon or alkali metals. Likewise, the powder may have no more than about 0.15 ppm/µC/g oxygen, and in some embodiments, no more than about 0.10 ppm/µC/g oxygen. Oxygen content may be measured by LECO Oxygen Analyzer and includes oxygen in natural oxide on the tantalum surface and bulk oxygen in the tantalum particles. Bulk oxygen content is controlled by period of crystalline lattice of tantalum, which is increasing linearly with increasing oxygen content in tantalum until the solubility limit is achieved. This method was described in "Critical Oxygen Content In Porous Anodes Of Solid Tantalum Capacitors", Pozdeev-Freeman et al., Journal of Materials Science: Materials In Electronics 9, (1998) 309-311 wherein X-ray diffraction analysis (XRDA) was employed to measure period of crystalline lattice of tantalum. Oxygen in sintered tantalum anodes may be limited to thin natural surface oxide, while the bulk of tantalum is practically free of oxygen.

To facilitate the construction of the anode, certain additional components may also be included in the powder. For example, the powder may be optionally mixed with a binder and/or lubricant to ensure that the particles adequately adhere to each other when compacted or pressed to form the pellet. Suitable binders may include, for instance, poly(vinyl butyral); poly(vinyl acetate); poly(vinyl alcohol); poly(vinyl pyrollidone); cellulosic polymers, such as carboxymethyl-cellulose, methyl cellulose, ethyl cellulose, hydroxyethyl cellulose, and methylhydroxyethyl cellulose; atactic polypropylene, polyethylene; polyethylene glycol (e.g., Carbowax from Dow Chemical Co.); polystyrene, poly(butadiene/styrene); polyamides, polyimides, and polyacrylamides, high molecular weight polyethers; copolymers of ethylene oxide and propylene oxide; fluoropolymers, such as polytetrafluoroethylene, polyvinylidene fluoride, and fluoroolefin copolymers; acrylic polymers, such as sodium polyacrylate, poly(lower alkyl acrylates), poly(lower alkyl methacrylates) and copolymers of lower alkyl acrylates and methacrylates; and fatty acids and waxes, such as stearic and other soapy fatty acids, vegetable wax, microwaxes (purified paraffins), etc. The binder may be dissolved and dispersed in a solvent. Exemplary solvents may include water, alcohols, and so forth. When utilized, the percentage of binders and/or lubricants may vary from about 0.1% to about 8% by weight of the total mass. It should be understood, however, that binders and/or lubricants are not necessarily required in the present invention.

The resulting powder may be compacted to form a pellet using any conventional powder press device. For example, a press mold may be employed that is a single station compaction press containing a die and one or multiple punches. Alternatively, anvil-type compaction press molds may be used that use only a die and single lower punch. Single station compaction press molds are available in several basic types, such as cam, toggle/knuckle and eccentric/crank presses with varying capabilities, such as single action, double action, floating die, movable platen, opposed ram, screw, impact, hot pressing, coining or sizing. The powder may be compacted around an anode lead wire. The wire may be formed from any electrically conductive material, such as tantalum, niobium, aluminum, hafnium, titanium, etc., as well as electrically conductive oxides and/or nitrides of thereof.

Any binder/lubricant may be removed after pressing by heating the pellet under vacuum at a certain temperature (e.g., from about 150° C. to about 500° C.) for several minutes. Alternatively, the binder/lubricant may also be removed by contacting the pellet with an aqueous solution, such as described in U.S. Pat. No. 6,197,252 to Bishop, et al. Thereafter, the pellet is sintered to form a porous, integral mass. The pellet is typically sintered at a temperature of from about 800° C. to about 2000° C., in some embodiments from about 1200° C. to about 1800° C., and in some embodiments, from about 1500° C. to about 1700° C., for a time of from about 5 minutes to about 100 minutes, and in some embodiments, from about 8 minutes to about 15 minutes. This may occur in one or more steps. If desired, sintering may occur in an atmosphere that limits the transfer of oxygen atoms to the anode. For example, sintering may occur in a reducing atmosphere, such as in a vacuum, inert gas, hydrogen, etc. The reducing atmosphere may be at a pressure of from about 10 Torr to about 2000 Torr, in some embodiments from about 100 Torr to about 1000 Torr, and in some embodiments, from about 100 Torr to about 930 Torr. Mixtures of hydrogen and other gases (e.g., argon or nitrogen) may also be employed.

Upon sintering, the pellet shrinks due to the growth of metallurgical bonds between the particles. Because shrinkage generally increases the density of the pellet, lower press densities ("green") may be employed to still achieve the desired target density. For example, the target density of the pellet after sintering is typically from about 5 to about 8 grams per cubic centimeter. As a result of the shrinking phenomenon, however, the pellet need not be pressed to such high densities, but may instead be pressed to densities of less than about 6.0 grams per cubic centimeter, and in some embodiments, from about 4.5 to about 5.5 grams per cubic centimeter. Among other things, the ability to employ lower green densities may provide significant cost savings and increase processing efficiency.

The thickness of the anode is generally small to improve the electrical performance and volumetric efficiency of the resulting capacitor. For example, the thickness of the anode may be about 5 millimeters or less, in some embodiments, from about 0.05 to about 4 millimeters, and in some embodiments, from about 0.1 to about 3.5 millimeters. The ratio of the length of the anode to the thickness of the anode is from about 5 to about 50, in some embodiments from about 6 to about 30, and in some embodiments, from about 7 to about 20. For example, the length of the anode may be from about 1 to about 80 millimeters, in some embodiments from about 10 to about 60 millimeters, and in some embodiments, from about 20 to about 50 millimeters. Further, the width of the anode may also be from about 0.05 to about 40 millimeters, in some embodiments, from about 0.5 to about 35 millimeters, and in some embodiments, from about 2 to about 25 millimeters. It should be understood that the anode may possess any desired shape, such as D-shaped, square, rectangle, circle, oval, triangle, etc. Polygonal shapes having more than four (4) edges (e.g., hexagon, octagon, heptagon, pentagon, etc.) are particularly desired due to their relatively high surface area.

The anode also contains a dielectric formed by anodically oxidizing ("anodizing") the sintered anode so that a dielectric layer is formed over and/or within the anode. For example, a tantalum (Ta) anode may be anodized to tantalum pentoxide ($Ta_2O_5$). Typically, anodization is performed by initially applying a solution to the anode, such as by dipping anode into the electrolyte. Aqueous solvents (e.g., water) and/or non-aqueous solvents (e.g., ethylene glycol) may be employed. To enhance conductivity, a compound may be employed that is capable of dissociating in the solvent to form ions. Examples of such compounds include, for instance, acids, such as described below with respect to the electrolyte. For example, an acid (e.g., phosphoric acid) may constitute from about 0.01 wt. % to about 5 wt. %, in some embodiments from about 0.05 wt. % to about 0.8 wt. %, and in some embodiments, from about 0.1 wt. % to about 0.5 wt. % of the anodizing solution. If desired, blends of acids may also be employed.

A current is passed through the anodizing solution to form the dielectric layer. The value of the formation voltage manages the thickness of the dielectric layer. For example, the power supply may be initially set up at a galvanostatic mode until the required voltage is reached. Thereafter, the power supply may be switched to a potentiostatic mode to ensure that the desired dielectric thickness is formed over the entire surface of the anode. Of course, other known methods may also be employed, such as pulse or step potentiostatic methods. The voltage at which anodic oxidation occurs is typically high to achieve a capacitor capable of operating at a high voltage range. That is, the voltage is typically from about 100 volts to about 300 volts, in some embodiments from about 170 volts to about 280 volts, and in some embodiments, from about 200 volts to about 250 volts. The temperature of the anodizing solution may range from about 10° C. to about 200° C., in some embodiments from about 20° C. to about 150° C., and in some embodiments, from about 30° C. to about 90° C. The resulting dielectric layer may be formed on a surface of the anode and within its pores. When employed, the specific nature of the powder may allow the resulting anode to achieve a high specific charge even at the high formation voltages often employed in the present invention.

II. Cathode

A. Metal Substrate

The cathode typically contains a metal substrate, which may also optionally serve as a casing for the capacitor. The substrate may be formed from a variety of different metals, such as tantalum, niobium, aluminum, nickel, hafnium, titanium, copper, silver, steel (e.g., stainless), alloys thereof, composites thereof (e.g., metal coated with electrically conductive oxide), and so forth. The geometric configuration of the substrate may generally vary as is well known to those skilled in the art, such as in the form of a foil, sheet, screen, container, can, etc. The metal substrate may form the all or a portion of casing for the capacitor, or it may simply be applied to the casing. Regardless, the substrate may have a variety of shapes, such as generally cylindrical, D-shaped, rectangular, triangular, prismatic, etc. If desired, a surface of the substrate may be roughened to increase its surface area and increase the degree to which a material may be able to adhere thereto. In one embodiment, for example, a surface of the substrate is chemically etched, such as by applying a solution of a corrosive substance (e.g., hydrochloric acid) to the surface. Mechanical roughening may also be employed. For instance, a surface of the substrate may be abrasive blasted by propelling a stream of abrasive media (e.g., sand) against at least a portion of a surface thereof.

B. Conductive Coating

A conductive coating may also be disposed on a surface of the metal substrate (e.g., interior surface) to serve as an electrochemically active material for the capacitor. Any number of layers may be employed in the coating. The materials employed in the coating may vary. For example, the conductive coating may contain a noble metal (e.g., ruthenium, rhodium, palladium, silver, osmium, iridium, platinum, gold, etc.), an oxide (e.g., ruthenium oxide), carbonaceous materials, conductive polymers, etc. In one embodiment, for example, the coating may include conductive polymer(s) that are typically π-conjugated and have electrical conductivity after oxidation or reduction. Examples of such π-conjugated conductive polymers include, for instance, polyheterocycles (e.g., polypyrroles, polythiophenes, polyanilines, etc.), polyacetylenes, poly-p-phenylenes, polyphenolates, and so forth. Substituted polythiophenes are particularly suitable for use as conductive polymer in that they have particularly good mechanical robustness and electrical performance. In one particular embodiment, the substituted polythiophene has the following general structure:

wherein,

T is O or S;

D is an optionally substituted $C_1$ to $C_5$ alkylene radical (e.g., methylene, ethylene, n-propylene, n-butylene, n-pentylene, etc.);

$R_7$ is a linear or branched, optionally substituted $C_1$ to $C_{18}$ alkyl radical (e.g., methyl, ethyl, n- or iso-propyl, n-, iso-, sec- or tert-butyl, n-pentyl, 1-methylbutyl, 2-methylbutyl, 3-methylbutyl, 1-ethylpropyl, 1,1-dimethylpropyl, 1,2-dimethylpropyl, 2,2-dimethylpropyl, n-hexyl, n-heptyl, n-octyl, 2-ethylhexyl, n-nonyl, n-decyl, n-undecyl, n-dodecyl, n-tridecyl, n-tetradecyl, n-hexadecyl, n-octadecyl, etc.); optionally substituted $C_5$ to $C_{12}$ cycloalkyl radical (e.g., cyclopentyl, cyclohexyl, cycloheptyl, cyclooctyl, cyclononyl cyclodecyl, etc.); optionally substituted $C_6$ to $C_{14}$ aryl radical (e.g., phenyl, naphthyl, etc.); optionally substituted $C_7$ to $C_{18}$ aralkyl radical (e.g., benzyl, o-, m-, p-tolyl, 2,3-, 2,4-, 2,5-, 2-6, 3-4-, 3,5-xylyl, mesityl, etc.); optionally substituted $C_1$ to $C_4$ hydroxyalkyl radical, or hydroxyl radical; and q is an integer from 0 to 8, in some embodiments, from 0 to 2, and in one embodiment, 0; and n is from 2 to 5,000, in some embodiments from 4 to 2,000, and in some embodiments, from 5 to 1,000. Example of substituents for the radicals "D" or "$R_7$" include, for instance, alkyl, cycloalkyl, aryl, aralkyl, alkoxy, halogen, ether, thioether, disulphide, sulfoxide, sulfone, sulfonate, amino, aldehyde, keto, carboxylic acid ester, carboxylic acid, carbonate, carboxylate, cyano, alkylsilane and alkoxysilane groups, carboxylamide groups, and so forth.

Particularly suitable thiophene polymers are those in which "D" is an optionally substituted $C_2$ to $C_3$ alkylene radical. For instance, the polymer may be optionally substituted poly(3,4-ethylenedioxythiophene), which has the following general structure:

Methods for forming conductive polymers, such as described above, are well known in the art. For instance, U.S. Pat. No. 6,987,663 to Merker, et al. describes various techniques for forming substituted polythiophenes from a monomeric precursor. The monomeric precursor may, for instance, have the following structure:

wherein,

T, D, $R_7$, and q are defined above. Particularly suitable thiophene monomers are those in which "D" is an optionally substituted $C_2$ to $C_3$ alkylene radical. For instance, optionally substituted 3,4-alkylenedioxythiophenes may be employed that have the general structure:

wherein, $R_7$ and q are as defined above. In one particular embodiment, "q" is 0. One commercially suitable example of 3,4-ethylenedioxthiophene is available from Heraeus Clevios under the designation Clevios™ M. Other suitable monomers are also described in U.S. Pat. No. 5,111,327 to Blohm, et al. and U.S. Pat. No. 6,635,729 to Groenendaal, et al. Derivatives of these monomers may also be employed that are, for example, dimers or trimers of the above monomers. Higher molecular derivatives, i.e., tetramers, pentamers, etc. of the monomers are suitable for use in the present invention. The derivatives may be made up of identical or different monomer units and used in pure form and in a mixture with one another and/or with the monomers. Oxidized or reduced forms of these precursors may also be employed.

The thiophene monomers may be chemically polymerized in the presence of an oxidative catalyst. The oxidative catalyst typically includes a transition metal cation, such as iron(III), copper(II), chromium(VI), cerium(IV), manganese (IV), manganese(VII), ruthenium(III) cations, etc. A dopant may also be employed to provide excess charge to the conductive polymer and stabilize the conductivity of the polymer. The dopant typically includes an inorganic or organic anion, such as an ion of a sulfonic acid. In certain embodiments, the oxidative catalyst employed in the precursor solution has both a catalytic and doping functionality in that it includes a cation (e.g., transition metal) and anion (e.g., sulfonic acid). For example, the oxidative catalyst may be a transition metal salt that includes iron(III) cations, such as iron(III) halides (e.g., $FeCl_3$) or iron(III) salts of other inorganic acids, such as $Fe(ClO_4)_3$ or $Fe_2(SO_4)_3$ and the iron(III) salts of organic acids and inorganic acids comprising organic radicals. Examples of iron (III) salts of inorganic acids with organic radicals include, for instance, iron(III) salts of sulfuric acid monoesters of $C_1$ to $C_{20}$ alkanols (e.g., iron(III) salt of lauryl sulfate). Likewise, examples of iron (III) salts of organic acids include, for instance, iron(III) salts of $C_1$ to $C_{20}$ alkane sulfonic acids (e.g., methane, ethane, propane, butane, or dodecane sulfonic acid); iron (III) salts of aliphatic perfluorosulfonic acids (e.g., trifluoromethane sulfonic acid, perfluorobutane sulfonic acid, or perfluorooctane sulfonic acid); iron (III) salts of aliphatic $C_1$ to $C_{20}$ carboxylic acids (e.g., 2-ethylhexylcarboxylic acid); iron (III) salts of aliphatic perfluorocarboxylic acids (e.g., trifluoroacetic acid or perfluorooctane acid); iron (III) salts of aromatic sulfonic acids optionally substituted by $C_1$ to $C_{20}$ alkyl groups (e.g., benzene sulfonic acid, o-toluene sulfonic acid, p-toluene sulfonic acid, or dodecylbenzene sulfonic acid); iron (III) salts of cycloalkane sulfonic acids (e.g., camphor sulfonic acid); and so forth. Mixtures of these above-mentioned iron(III) salts may also be used. Iron(III)-p-toluene sulfonate, iron(III)-o-toluene sulfonate, and mixtures thereof, are particularly suitable. One commercially suitable example of iron(III)-p-toluene sulfonate is available from Heraeus Clevios under the designation Clevios™ C.

Various methods may be utilized to form the conductive layer. In one embodiment, the oxidative catalyst and monomer are applied, either sequentially or together, such that the polymerization reaction occurs in situ on the substrate. Suitable application techniques may include screen-printing, dipping, electrophoretic coating, and spraying, may be used to form a conductive polymer coating. As an example, a monomer may initially be mixed with the oxidative catalyst to form a precursor solution. Once the mixture is formed, it may be applied to the metal substrate and then allowed to polymerize so that the conductive layer is formed. Alternatively, the oxidative catalyst and monomer may be applied sequentially. In one embodiment, for example, the oxidative catalyst is dissolved in an organic solvent (e.g., butanol) and then applied as a dipping solution. The substrate may then be dried to remove the solvent therefrom. Thereafter, the substrate may be dipped into a solution containing the monomer. Polymerization is typically performed at temperatures of from about −10° C. to about 250° C., and in some embodiments, from about 0° C. to about 200° C., depending on the oxidizing agent used and desired reaction time. Suitable polymerization techniques, such as described above, may be described in more detail in U.S. Publication No. 2008/232037 to Biler.

While chemical polymerization techniques may be employed in certain embodiments, it is often desired to minimize the use of oxidative catalysts in the capacitor as such materials can often lead to the formation of iron radicals (e.g., $Fe^{2+}$ or $Fe^{3+}$ ions). These radicals can, in turn, lead to dielectric degradation at the high voltages often employed during the use of the wet capacitor. Thus, anodic electrochemical polymerization techniques may be employed in certain embodiments to form the conductive polymer. Such techniques generally employ a colloidal suspension that is generally free of iron-based oxidative catalysts. For instance, the colloidal suspension typically contains less than about 0.5 wt. %, in some embodiments, less than about 0.1 wt. %, and in some embodiments, less than about 0.05 wt. % (e.g., 0 wt. %) of such iron-based oxidative catalysts.

The colloidal suspension may be in the form of a macroemulsion, microemulsion, solution, etc. depending on the particular nature of the components of the suspension. Regardless, the suspension generally contains a solvent that serves as a continuous phase within which the precursor monomer is dispersed. Any of a variety of different solvents may be employed in the colloidal suspension, such as alcohols, glycols, water, etc. In one particular embodiment, the colloidal suspension is aqueous in nature. If desired, other additives may also be employed in the suspension to facilitate polymerization, such as surfactants (e.g., nonionic, anionic, or cationic surfactants), dopants (e.g., sulfonic acids), defoaming agents, and so forth. Solvents (e.g., water) may constitute from about 50 wt. % to about 99 wt. %, in some embodiments from about 70 wt. % to about 98 wt. % and in some embodiments, from about 80 wt. % to about 95 wt. %. The remaining components of the colloidal suspension (e.g., precursor monomers, surfactants, and sulfonic acids) may likewise constitute from about 1 wt. % to about 50 wt. %, in some embodiments from about 2 wt. % to about 30 wt. % and in some embodiments, from about 5 wt. % to about 20 wt. % of the colloidal suspension.

To apply the colloidal suspension, any of a variety of suitable application techniques may be employed, such as screen-printing, dipping, electrophoretic coating, spraying, etc. Regardless of how it is applied, the monomer within the colloidal suspension may be anodically electrochemically-polymerized to form the conductive polymer layer. In one embodiment, for example, the metal substrate is dipped into a bath containing the colloidal suspension of the present invention. A pair of electrodes may be disposed within the bath for electrolysis. One electrode may be connected to the positive terminal of a power source and also in contact with the metal substrate. The other electrode may be connected to the negative terminal of the power source and an additional inert metal. During operation, the power source supplies a current feed to the electrodes in the electrochemical cell, thereby inducing electrolysis of the electrolyte and oxidative polymerization of the monomer in the colloidal suspension, or solution, onto the metal substrate. Anodic electrochemical polymerization is generally performed at ambient temperature to ensure that the colloidal suspension does not phase separate. For example, the colloidal suspension may be kept at a temperature of from about 15° C. to about 80° C., in some embodiments from about 20° C. to about 75° C., and in some embodiments, from about 25° C. to about 50° C. The amount of time in which the metal substrate is in contact with the colloidal suspension during anodic electrochemical polymerization may vary. For example, the metal substrate may be dipped into such a solution for a period of time ranging from about 10 seconds to about 10 minutes.

Multiple polymerization steps may be repeated until the desired thickness of the coating is achieved. In one embodiment, for example, a chemically polymerized layer may be formed directly over the noble metal layer and an electrochemical polymerized layer may be disposed thereover, or vice versa. Regardless, the total target thickness of the conductive polymer layer(s) may generally vary depending on the desired properties of the capacitor. Typically, the resulting conductive polymer layer(s) have a thickness of from about 0.2 micrometers ("µm") to about 50 µm, in some embodiments from about 0.5 µm to about 20 µm, and in some embodiments, from about 1 µm to about 5 µm. It should be understood that the thickness of the layers are not necessarily the same at all locations on the substrate. Nevertheless, the average thickness on the substrate generally falls within the ranges noted above.

III. Microporous Membrane

Generally speaking, the microporous membrane contains a plurality of pores that allow for ionic transport. Typically, the average size of such pores is about 1 micrometer or less, in some embodiments about 500 nanometers or less, and in some embodiments, from about 1 to about 100 nanometers. Regardless, the membrane is formed form a polymeric material that contains an olefin polymer. The olefin polymer may be a homopolymers or copolymer of one or more olefins, such as ethylene, propylene, 1-butene, 4-methyl-1-pentene, and 1-hexene, etc., as well as combinations thereof. In certain embodiments, for example, the olefin polymer is a homopolymer, as such polyethylene. Of course, the olefin polymer may also be a copolymer of ethylene or propylene, for instance, with another α-olefin, such as a $C_3$-$C_{20}$ α-olefin. Specific examples of suitable α-olefins include 1-butene; 3-methyl-1-butene; 3,3-dimethyl-1-butene; 1-pentene; 1-pentene with one or more methyl, ethyl or propyl substituents; 1-hexene with one or more methyl, ethyl or propyl substituents; 1-heptene with one or more methyl, ethyl or propyl substituents; 1-octene with one or more methyl, ethyl or propyl substituents; 1-nonene with one or more methyl, ethyl or propyl substituents; ethyl, methyl or dimethyl-substituted 1-decene; 1-dodecene; and styrene. Ultra-high molecular weight polyethylene ("UHMWPE") is particularly suitable. Typically, the olefin polymers have a high melting temperature, such as about 105° C. or more, in some embodiments about 115° C. or more, and in some embodiments, from about 130° C. to about 160° C. (e.g., 135° C.). If desired, the polymeric material may also contain one or more additives, such as a heat resistance-stabilizing agent, weather resistance-stabilizing agent, antistatic agent, anti-blocking agent, slip agent, lubricant, nucleating agent, pigment, filler, flame retardant, etc.

The membrane may be formed using techniques well known in the art. In one embodiment, for example, an olefin polymer powder may be compacted to form a preform material that may then be sintered (e.g., in a water vapor atmosphere). The average particle diameter of the powder may vary, but is typically about 250 micrometers or less, in some embodiments from about 0.1 to about 150 micrometers, and in some embodiments, from about 0.5 to about 100 micrometers. Sintering may likewise occur at a temperature at or above the melting temperature, such as at a temperature of about 130° C. or more, in some embodiments about 140° C. or more, and in some embodiments, from about 150° C. to about 190° C. (e.g., 180° C.). After sintering, a pellet body is formed that may optionally be cut into sheet form to create the microporous membrane structure. If desired, the sheet may also stretched in one or more directions as is known in the art.

IV. Working Electrolyte

The working electrolyte may be in electrical communication with the cathode and anode. The electrolyte is a fluid that may be impregnated within the anode, or it may be added to the capacitor at a later stage of production. The fluid electrolyte generally uniformly wets the dielectric on the anode. Various suitable electrolytes are described in U.S. Pat. Nos. 5,369,547 and 6,594,140 to Evans, et al. Typically, the electrolyte is ionically conductive in that has an electrical conductivity of from about 0.1 to about 20 Siemens per centimeter ("S/cm"), in some embodiments from about 0.2 to about 15 S/cm, and in some embodiments, from about 0.5 to about 10 S/cm, determined at a temperature of about 23° C. using any known electric conductivity meter (e.g., Oakton Con Series 11). The fluid electrolyte is generally in the form of a liquid, such as a solution (e.g., aqueous or non-aqueous), colloidal suspension, gel, etc. For example, the electrolyte may be an aqueous solution of an acid (e.g., sulfuric acid, phosphoric acid, or nitric acid), base (e.g., potassium hydroxide), or salt (e.g., ammonium salt, such as a nitrate), as well any other suitable electrolyte known in the art, such as a salt dissolved in an organic solvent (e.g., ammonium salt dissolved in a glycol-based solution). Various other electrolytes are described in U.S. Pat. Nos. 5,369, 547 and 6,594,140 to Evans, et al.

The desired ionic conductivity may be achieved by selecting ionic compound(s) (e.g., acids, bases, salts, and so forth) within certain concentration ranges. In one particular embodiment, salts of weak organic acids may be effective in achieving the desired conductivity of the electrolyte. The cation of the salt may include monatomic cations, such as alkali metals (e.g., $Li^+$, $Na^+$, $K^+$, $Rb^+$, or $Cs^+$), alkaline earth metals (e.g., $Be^{2+}$, $Mg^{2+}$, $Ca^{2+}$, $Sr^{2+}$ or $Ba^{2+}$), transition metals (e.g., $Ag^+$, $Fe^{2+}$, $Fe^{3+}$, etc.), as well as polyatomic cations, such as $NH_4^+$. The monovalent ammonium ($NH_4^+$), sodium ($K^+$), and lithium ($Li^+$) are particularly suitable cations for use in the present invention. The organic acid used to form the anion of the salt may be "weak" in the sense that it typically has a first acid dissociation constant ($pK_{a1}$) of about 0 to about 11, in some embodiments about 1 to about 10, and in some embodiments, from about 2 to about 10, determined at about 23° C. Any suitable weak organic acids may be used in the present invention, such as carboxylic acids, such as acrylic acid, methacrylic acid, malonic acid, succinic acid, salicylic acid, sulfosalicylic acid, adipic acid, maleic acid, malic acid, oleic acid, gallic acid, tartaric acid (e.g., dextotartaric acid, mesotartaric acid, etc.), citric acid, formic acid, acetic acid, glycolic acid, oxalic acid, propionic acid, phthalic acid, isophthalic acid, glutaric acid, gluconic acid, lactic acid, aspartic acid, glutaminic acid, itaconic acid, trifluoroacetic acid, barbituric acid, cinnamic acid, benzoic acid, 4-hydroxybenzoic acid, aminobenzoic acid, etc.; blends thereof, and so forth. Polyprotic acids (e.g., diprotic, triprotic, etc.) are particularly desirable for use in forming the salt, such as adipic acid ($pK_{a1}$ of 4.43 and $pK_{a2}$ of 5.41), α-tartaric acid ($pK_{a1}$ of 2.98 and $pK_{a2}$ of 4.34), meso-tartaric acid ($pK_{a1}$ of 3.22 and $pK_{a2}$ of 4.82), oxalic acid ($pK_{a1}$ of 1.23 and $pK_{a2}$ of 4.19), lactic acid ($pK_{a1}$ of 3.13, $pK_{a2}$ of 4.76, and $pK_{a3}$ of 6.40), etc.

While the actual amounts may vary depending on the particular salt employed, its solubility in the solvent(s) used in the electrolyte, and the presence of other components, such weak organic acid salts are typically present in the electrolyte in an amount of from about 0.1 to about 25 wt. %, in some embodiments from about 0.2 to about 20 wt. %, in some embodiments from about 0.3 to about 15 wt. %, and in some embodiments, from about 0.5 to about 5 wt. %.

The electrolyte is typically aqueous in that it contains an aqueous solvent, such as water (e.g., deionized water). For example, water (e.g., deionized water) may constitute from about 20 wt. % to about 95 wt. %, in some embodiments from about 30 wt. % to about 90 wt. %, and in some embodiments, from about 40 wt. % to about 85 wt. % of the electrolyte. A secondary solvent may also be employed to form a solvent mixture. Suitable secondary solvents may include, for instance, glycols (e.g., ethylene glycol, propylene glycol, butylene glycol, triethylene glycol, hexylene glycol, polyethylene glycols, ethoxydiglycol, dipropyleneglycol, etc.); glycol ethers (e.g., methyl glycol ether, ethyl glycol ether, isopropyl glycol ether, etc.); alcohols (e.g., methanol, ethanol, n-propanol, iso-propanol, and butanol); ketones (e.g., acetone, methyl ethyl ketone, and methyl isobutyl ketone); esters (e.g., ethyl acetate, butyl acetate, diethylene glycol ether acetate, methoxypropyl acetate, ethylene carbonate, propylene carbonate, etc.); amides (e.g., dimethylformamide, dimethylacetamide, dimethylcaprylic/capric fatty acid amide and N-alkylpyrrolidones); sulfoxides or sulfones (e.g., dimethyl sulfoxide (DMSO) and sulfolane); and so forth. Such solvent mixtures typically contain water in an amount from about 40 wt. % to about 80 wt. %, in some embodiments from about 50 wt. % to about 75 wt. %, and in some embodiments, from about 55 wt. % to about 70 wt. % and secondary solvent(s) in an amount from about 20 wt. % to about 60 wt. %, in some embodiments from about 25 wt. % to about 50 wt. %, and in some embodiments, from about 30 wt. % to about 45 wt. %. The secondary solvent(s) may, for example, constitute from about 5 wt. % to about 45 wt. %, in some embodiments from about 10 wt. % to about 40 wt. %, and in some embodiments, from about 15 wt. % to about 35 wt. % of the electrolyte.

If desired, the electrolyte may be relatively neutral and have a pH of from about 4.5 to about 8.0, in some embodiments from about 5.0 to about 7.5, and in some embodiments, from about 5.5 to about 7.0. One or more pH adjusters (e.g., acids, bases, etc.) may be employed to help achieve the desired pH. In one embodiment, an acid is employed to lower the pH to the desired range. Suitable acids include, for instance, organic acids such as described above; inorganic acids, such as hydrochloric acid, nitric acid, sulfuric acid, phosphoric acid, polyphosphoric acid, boric acid, boronic acid, etc.; and mixtures thereof. Although the total concentration of pH adjusters may vary, they are typically present in an amount of from about 0.01 wt. % to about 10 wt. %, in some embodiments from about 0.05 wt. % to about 5 wt. %, and in some embodiments, from about 0.1 wt. % to about 2 wt. % of the electrolyte.

The electrolyte may also contain other components that help improve the electrical performance of the capacitor. For instance, a depolarizer may be employed in the electrolyte to help inhibit the evolution of hydrogen gas at the cathode of the electrolytic capacitor, which could otherwise cause the capacitor to bulge and eventually fail. When employed, the depolarizer normally constitutes from about 1 to about 500 parts per million ("ppm"), in some embodiments from about 10 to about 200 ppm, and in some embodiments, from about 20 to about 150 ppm of the electrolyte. Suitable depolarizers may include nitroaromatic compounds, such as 2-nitrophenol, 3-nitrophenol, 4-nitrophenol, 2-nitrobenzonic acid, 3-nitrobenzonic acid, 4-nitrobenzonic acid, 2-nitroacetophenone, 3-nitroacetophenone, 4-nitroacetophenone, 2-nitroanisole, 3-nitroanisole, 4-nitroanisole, 2-nitrobenzaldehyde, 3-nitrobenzaldehyde, 4-nitrobenzaldehyde, 2-nitrobenzyl alcohol, 3-nitrobenzyl alcohol, 4-nitrobenzyl alcohol, 2-nitrophthalic acid, 3-nitrophthalic acid, 4-nitrophthalic acid, and so forth. Particularly suitable nitroaromatic depolarizers for use in the present invention are nitrobenzoic acids, anhydrides or salts thereof, substituted with one or more alkyl groups (e.g., methyl, ethyl, propyl, butyl, etc.). Specific examples of such alkyl-substituted nitrobenzoic compounds include, for instance, 2-methyl-3-nitrobenzoic acid; 2-methyl-6-nitrobenzoic acid; 3-methyl-2-nitrobenzoic acid; 3-methyl-4-nitrobenzoic acid; 3-methyl-6-nitrobenzoic acid; 4-methyl-3-nitrobenzoic acid; anhydrides or salts thereof; and so forth.

Figure 1:
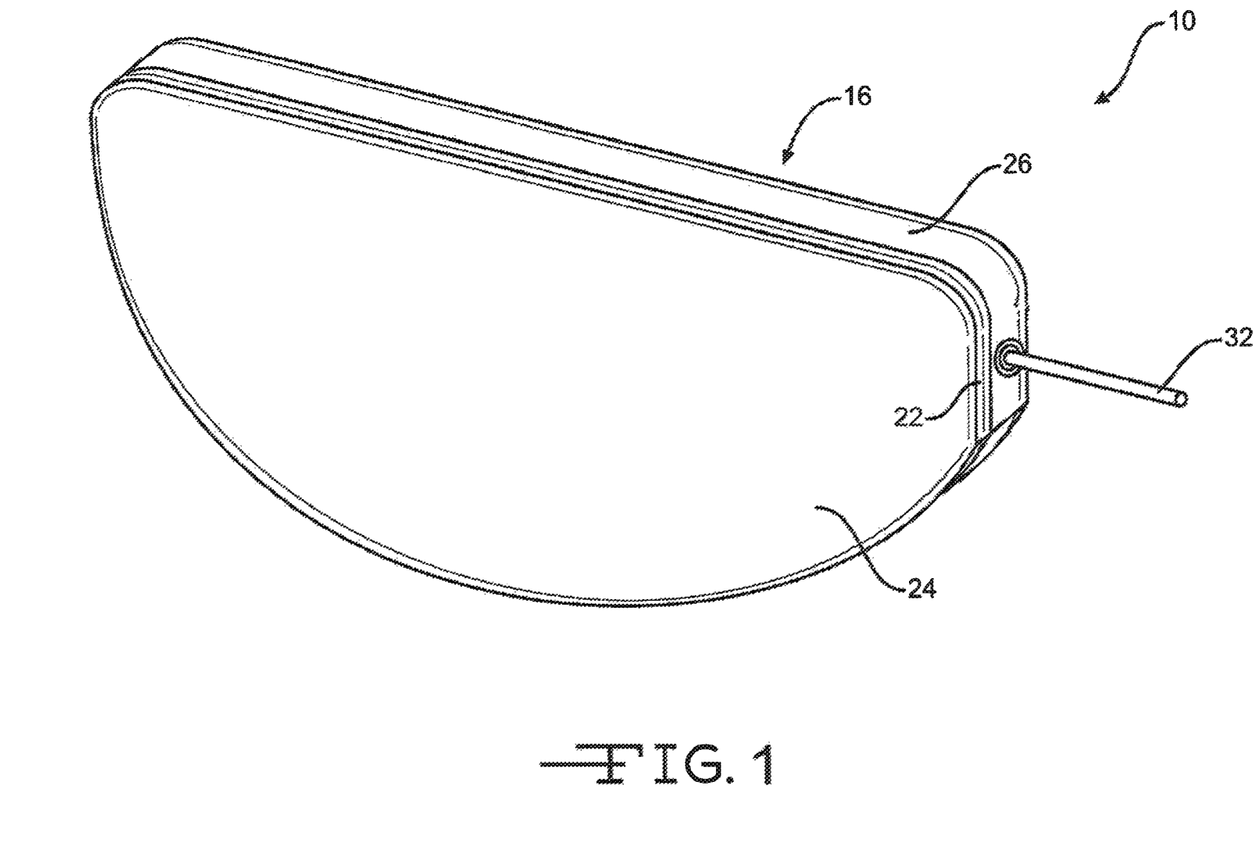
FIG. 1 is a perspective view of one embodiment of the capacitor of the present invention.
Figure 2:
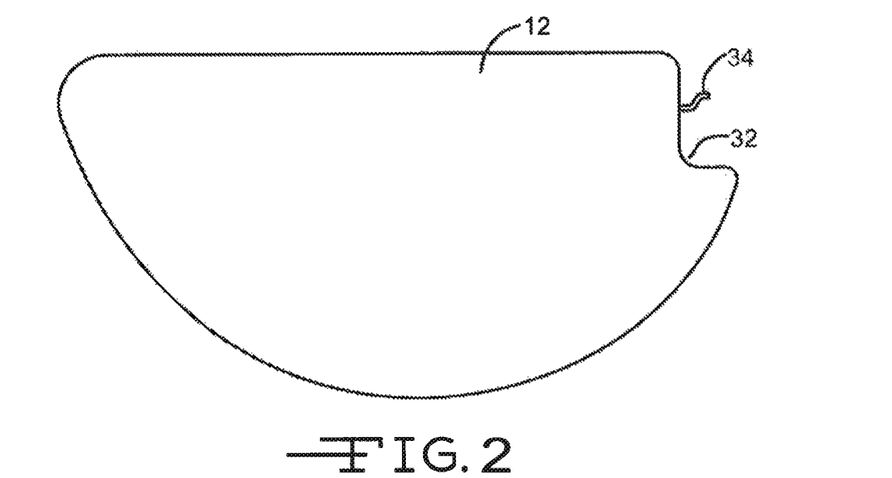
FIG. 2 is a side view of embodiment of an anode that may be employed in the capacitor of the present invention.
Figure 3:
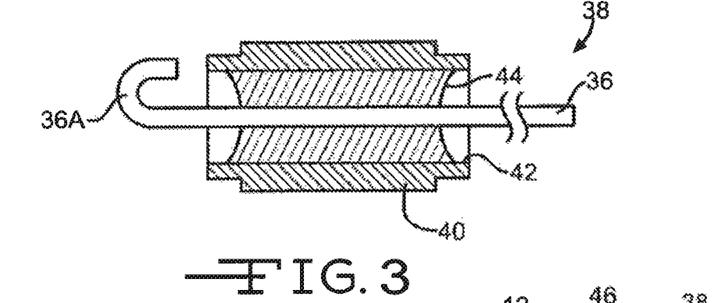
FIG. 3 is a cross-sectional view showing one embodiment of a seal that may be employed in the capacitor of the present invention.
Figure 4:
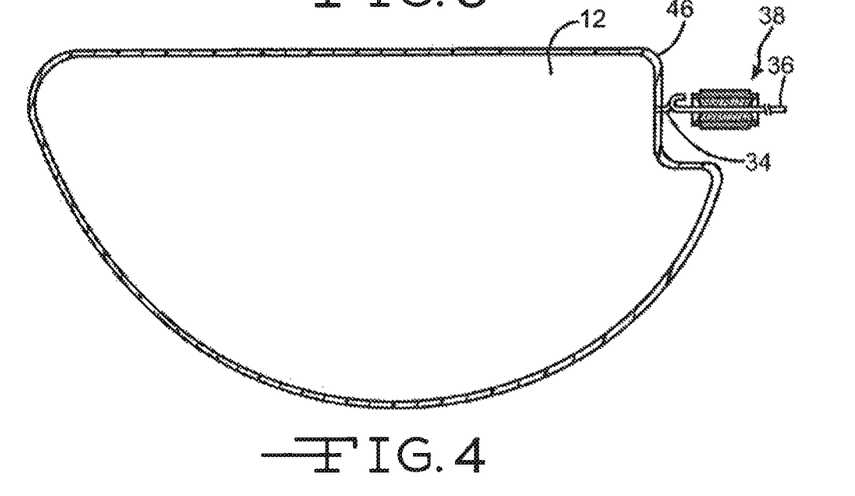
FIG. 4 is a side view showing one embodiment of an anode and separator that may be employed in the capacitor of the present invention.

The particular manner in which the components are incorporated into the capacitor is not critical and may be accomplished using a variety of techniques. In most embodiments, however, the anode is positioned within a casing. Referring to FIGS. 1-4, for example, one embodiment of a capacitor 10 is shown that includes an anode 12, microporous membrane 46, and working electrolyte (not shown) that can be hermetically sealed within a casing 16. Although only one anode and microporous membrane are shown, it should be understood that multiple anodes (e.g., stack) and/or membranes may be employed. For example, a first membrane may be positioned on one side of the anode while a second membrane may be positioned on the opposing side of the anode. One or both membranes may be formed in accordance with the present invention. Alternatively, a single microporous membrane may simply be wrapped around the anode. In the illustrated embodiment, for instance, the membrane 46 is in the shape of a bag that completely surrounds and envelops the anode 12.

In this embodiment, the casing 16 contains first and second casing portions 18 and 20. The casing portion 18 contains a surrounding sidewall 22 extending to a face wall 24 and the casing portion 20 likewise includes a surrounding sidewall 26 extending to a face wall (now shown). A cathode conductive coating (not shown) may be located on the face walls to form the cathode active material. The coating may be either directly located on the inner surface of the face wall such that the casing itself forms the metal substrate of the cathode. Alternatively, the coating may be located on a separate metal substrate (not shown) in electrical contact with the inner surface of the face wall. Once the anode 12 and the membrane 26 are located within the casing, the casing portions 18 and 20 may be hermetically sealed together by welding the overlapping sidewalls 22 and 26 where they contact. The weld may be provided by any conventional technique, such as laser welding. Although by no means required, the anode 12 may have a notch 32 from an anode wire 34 extends as described above. The wire 34 may be connected to an anode lead 36 supported by an insulative seal 38. The seal 38 may contain a ferrule 40 defining an internal cylindrical through bore or passage 42 of a constant inside diameter. An insulative material 44 (e.g., glass) provides the hermetic seal between the bore 42 and the anode lead 36 passing therethrough. The anode lead 36 has a J-shaped proximal portion 36A that is subsequently connected to a crook in the anode wire 34, such as by laser welding, to secure them together. After assembly and sealing (e.g., welding), the working electrolyte may optionally be introduced into the casing through a fill-port. Filling may be accomplished by placing the capacitor in a vacuum chamber so that the fill-port extends into a reservoir of the electrolyte. When the chamber is evacuated, pressure is reduced inside the capacitor. When the vacuum is released, pressure inside the capacitor re-equilibrates, and the electrolyte is drawn through the fill-port into the capacitor. Alternatively, the working electrolyte may be included within the housing prior to sealing, such as by saturating the membrane with the electrolyte before it is inserted into the casing.

Regardless of its particular configuration, the capacitor of the present invention may exhibit excellent electrical properties. For example, the capacitor may exhibit a high volumetric efficiency, such as from about 50,000 $\mu F*V/cm^3$ to about 300,000 $\mu F*V/cm^3$, in some embodiments from about 60,000 $\mu F*V/cm^3$ to about 200,000 $\mu F*V/cm^3$, and in some embodiments, from about 80,000 $\mu F*V/cm^3$ to about 150,000 $\mu F*V/cm^3$, determined at a frequency of 120 Hz and at room temperature (e.g., 25° C.). Volumetric efficiency is determined by multiplying the formation voltage of a part by its capacitance, and then dividing by the product by the volume of the part. For example, a formation voltage may be 175 volts for a part having a capacitance of 520 $\mu F$, which results in a product of 91,000 $\mu F*V$. If the part occupies a volume of about 0.8 $cm^3$, this results in a volumetric efficiency of about 113,750 $\mu F*V/cm^3$.

The capacitor may also exhibit a high energy density that enables it suitable for use in high pulse applications. Energy density is generally determined according to the equation $E=\frac{1}{2}*CV^2$, where C is the capacitance in farads (F) and V is the working voltage of capacitor in volts (V). The capacitance may, for instance, be measured using a capacitance meter (e.g., Keithley 3330 Precision LCZ meter with Kelvin Leads, 2 volts bias and 1 volt signal) at operating frequencies of from 10 to 120 Hz (e.g., 120 Hz) and a temperature of 25° C. For example, the capacitor may exhibit an energy density of about 2.0 joules per cubic centimeter ($J/cm^3$) or more, in some embodiments about 3.0 $J/cm^3$, in some embodiments from about 3.5 $J/cm^3$ to about 10.0 $J/cm^3$, and in some embodiments, from about 4.0 to about 8.0 $J/cm^3$. The capacitance may likewise be about 1 milliFarad per square centimeter ("$mF/cm^2$") or more, in some embodiments about 2 $mF/cm^2$ or more, in some embodiments from about 5 to about 50 $mF/cm^2$, and in some embodiments, from about 8 to about 20 $mF/cm^2$. The capacitor may also exhibit a relatively high "breakdown voltage" (voltage at which the capacitor fails), such as about 180 volts or more, in some about 200 volts or more, and in some embodiments, from about 210 volts to about 260 volts.

The equivalent series resistance ("ESR")—the extent that the capacitor acts like a resistor when charging and discharging in an electronic circuit—may also be less than about 15,000 milliohms, in some embodiments less than about 10,000 milliohms, in some embodiments less than about 5,000 milliohms, and in some embodiments, from about 1 to about 4,500 milliohms, measured with a 2-volt bias and 1-volt signal at a frequency of 120 Hz. In addition, the leakage current, which generally refers to the current flowing from one conductor to an adjacent conductor through an insulator, can be maintained at relatively low levels. For example, the numerical value of the normalized leakage current of a capacitor of the present invention is, in some embodiments, less than about 1 $\mu A/\mu F*V$, in some embodiments less than about 0.5 $\mu A/\mu F*V$, and in some embodiments, less than about 0.1 $\mu A/\mu F*V$, where $\mu A$ is microamps and $\mu F*V$ is the product of the capacitance and the rated voltage. Leakage current may be measured using a leakage test meter (e.g., MC 190 Leakage test, Mantracourt Electronics LTD, UK) at a temperature of 25° C. and at a certain rated voltage after a charging time of from about 60 to about 300 seconds. Such ESR and normalized leakage current values may even be maintained after aging for a substantial amount of time at high temperatures. For example, the values may be maintained for about 100 hours or more, in some embodiments from about 300 hours to about 2500 hours, and in some embodiments, from about 400 hours to about 1500 hours (e.g., 500 hours, 600 hours, 700 hours, 800 hours, 900 hours, 1000 hours, 1100 hours, or 1200 hours) at temperatures ranging from about 100° C. to about 250° C., and, in some embodiments from about 100° C. to about 200° C. (e.g., 100° C., 125° C., 150° C., 175° C., or 200° C.).

The electrolytic capacitor of the present invention may be used in various applications, including but not limited to implantable medical devices, such as implantable defibrillators, pacemakers, cardioverters, neural stimulators, drug administering devices, etc. In one embodiment, for example, the capacitor may be employed in an implantable medical device configured to provide a therapeutic high voltage (e.g., between approximately 500 volts and approximately 850 volts, or, desirably, between approximately 600 Volts and approximately 900 volts) treatment for a patient. The device may contain a container or housing that is hermetically sealed and biologically inert. One or more leads are electrically coupled between the device and the patient's heart via a vein. Cardiac electrodes are provided to sense cardiac activity and/or provide a voltage to the heart. At least a portion of the leads (e.g., an end portion of the leads) may be provided adjacent or in contact with one or more of a ventricle and an atrium of the heart. The device may also contain a capacitor bank that typically contains two or more capacitors connected in series and coupled to a battery that is internal or external to the device and supplies energy to the capacitor bank. Due in part to high conductivity, the capacitor of the present invention can achieve excellent electrical properties and thus be suitable for use in the capacitor bank of the implantable medical device.

The present invention may be better understood by reference to the following example.

Test Procedures

Capacitance ("CAP"), equivalent series resistance ("ESR") and leakage current ("DCL") may be tested in an aqueous neutral electrolyte at a temperature of 37° C.±0.5° C.

Capacitance ("CAP")

Capacitance may be measured using a Keithley 3330 Precision LCZ meter with Kelvin Leads with 2.2 volt DC bias and a 0.5 volt peak to peak sinusoidal signal. The operating frequency may be 120 Hz.

Equivalent Series Resistance ("ESR")

Equivalence series resistance may be measured using a Keithley 3330 Precision LCZ meter with Kelvin Leads 2.2 volt DC bias and a 0.5 volt peak to peak sinusoidal signal. The operating frequency may be 120 Hz.

Leakage Current ("DCL")

Leakage current may be determined by charging to 250V for 300 seconds without any resistor in series.

These and other modifications and variations of the present invention may be practiced by those of ordinary skill in the art, without departing from the spirit and scope of the present invention. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed is:

1. A wet electrolytic capacitor comprising:
    an anode that comprises an anodically oxidized pellet formed from a pressed and sintered valve metal powder;
    a cathode that comprises a metal substrate coated with a conductive coating;
    a microporous membrane comprising a plurality of pores that is positioned between the anode and cathode, wherein the microporous membrane contains an olefin polymer having a weight-average molecular weight of about 1,000,000 grams per mole or more, wherein the plurality of pores have an average size of about 1 micrometer or less, and wherein the microporous membrane is free of surfactants; and
    a fluidic working electrolyte in communication with the anode and the cathode.

2. The wet electrolytic capacitor of claim 1, wherein the olefin polymer is polyethylene.

3. The wet electrolytic capacitor of claim 1, wherein the membrane is formed from a sintered powder.

4. The wet electrolytic capacitor of claim 1, wherein the membrane exhibits a tensile strength of about 30 Megapascals or more in both the machine direction and the transverse direction.

5. The wet electrolytic capacitor of claim 1, wherein the membrane has a thickness of about 100 micrometers or less.

6. The wet electrolytic capacitor of claim 1, wherein the ratio of the total thickness of the capacitor to the thickness of the microporous membrane is about 5 or more.

7. The wet electrolytic capacitor of claim 1, wherein the anode is enveloped within the microporous membrane.

8. The wet electrolytic capacitor of claim 1, wherein the anode is positioned between separate microporous membranes, at least one of which contains the olefin polymer having a weight-average molecular weight of about 1,000,000 grams per mole or more.

9. The capacitor of claim 1, wherein the anode contains tantalum pentoxide.

10. The capacitor of claim 1, wherein the valve metal powder includes tantalum.

11. The capacitor of claim 1, wherein the valve metal powder contains particles having an aspect ratio of about 4 or less.

12. The capacitor of claim 11, wherein the particles are nodular or angular particles.

13. The capacitor of claim 1, wherein the valve metal powder contains particles having a median size of from about 5 to about 1000 nanometers.

14. The capacitor of claim 1, wherein the powder has a specific charge of about 15,000 µF*V/g or more.

15. The capacitor of claim 1, wherein the powder has no more than about 50 ppm of alkali metals.

16. The capacitor of claim 1, wherein a leadwire extends from the anode.

17. The capacitor of claim 1, wherein the anode has a D-shape.

18. The capacitor of claim 1, wherein the metal substrate includes titanium or stainless steel.

19. The capacitor of claim 1, wherein the conductive coating includes a substituted polythiophene.

20. The capacitor of claim 1, wherein the electrolyte has a pH of from about 5.0 to about 7.5.

21. The capacitor of claim 1, wherein the capacitor contains a casing that contains a first casing member and a second casing member between which the anode and the fluid working electrolyte are disposed, wherein the metal substrate forms at least a portion of the first casing member, the second casing member, or both.

22. The capacitor of claim 21, wherein the first casing member contains a face wall and a surrounding sidewall that extends to an edge, and further wherein the second casing member is sealed to the edge of the sidewall.

23. An implantable medical device comprising the capacitor of claim 1.

* * * * *